US006390994B1

(12) United States Patent
Guanche et al.

(10) Patent No.: US 6,390,994 B1
(45) Date of Patent: May 21, 2002

(54) SHOULDER ARTHROMETER

(76) Inventors: Carlos A. Guanche, 11061 Bluestem La., Eden Prairie, MN (US) 55347; Joseph E. Hale, 2976 Furness St. North, Mapplewood, MN (US) 55109

( * ) Notice: Subject to any disclaimer, the term of this patent is extended or adjusted under 35 U.S.C. 154(b) by 0 days.

(21) Appl. No.: 09/721,823

(22) Filed: Nov. 24, 2000

(51) Int. Cl.$^7$ ............................................. A61B 5/103
(52) U.S. Cl. ...................................... 600/587
(58) Field of Search ............................. 600/587, 594, 600/595

(56) References Cited

U.S. PATENT DOCUMENTS

| | | | |
|---|---|---|---|
| 4,583,554 A | 4/1986 | Mittelman et al. | 128/774 |
| 4,583,555 A | 4/1986 | Malcom et al. | 128/782 |
| 4,667,685 A | 5/1987 | Fine | 128/782 |
| 4,883,069 A | 11/1989 | McLeod | 128/774 |
| 4,913,163 A | 4/1990 | Roger | 128/782 |
| 4,969,471 A | 11/1990 | Daniel et al. | 128/774 |
| 5,042,505 A | 8/1991 | Mayer et al. | 128/781 |
| 5,228,454 A | 7/1993 | Siegler | 128/782 |
| 5,253,655 A | 10/1993 | Stone et al. | 128/782 |
| 5,263,492 A | 11/1993 | Voyce | 128/782 |
| 5,291,901 A | 3/1994 | Graf | 128/781 |
| 5,313,968 A | 5/1994 | Logan et al. | 128/782 |
| 5,316,018 A | 5/1994 | O'Brien | 128/782 |
| 5,335,674 A | 8/1994 | Siegler | 128/782 |
| 5,402,800 A | 4/1995 | Hollis | 128/779 |
| 5,474,088 A | 12/1995 | Zaharkin et al. | 128/782 |
| 5,647,375 A | 7/1997 | Farfan De Los Godos | 128/781 |
| 5,911,695 A | 6/1999 | Watkins et al. | 600/587 |

OTHER PUBLICATIONS

Krarup et al, Journal of Shoulder and Elbow Surgery, vol. 8, pp. 136–141.

Jorgensen et al, Knee Surg Sports Traumatol (1999) 7, pp. 118–124.

Rockwood, Jr et al, The Shoulder, vol. 1, 1990, pp. 149–177.

Rockwood, Jr et al, The Shoulder, vol. 1, 1990, pp. 526, 547–551.

Jorgensen et al, Acta Orthop Scand 1995: 66(5), pp. 398–400.

Ganz, J Bone Joint Surgery, 1984, vol. 66–B, No. 4, pp. 551–556.

Sidles et al, 37$^{th}$ Annual MTG, Orthopaedic Research Soc, Mar. 4–7, 1991, p 646.*

* cited by examiner

Primary Examiner—Kevin Shaver
Assistant Examiner—Pamela Wingood
(74) Attorney, Agent, or Firm—Lawrence N. Ginsberg

(57) ABSTRACT

A shoulder arthrometer for measuring glenohumeral joint translation upon application of a force to an arm of a patient. It includes an arm attachment assembly, a force measurement gauge, a translation measurement gauge assembly, and a girdle assembly. The arm attachment assembly is capable of being secured to the arm of a patient. The force measurement gauge is operably engaged with the arm attachment assembly for measuring a force applied to the arm attachment assembly in anterior-posterior directions and the inferior direction. The translation measurement gauge assembly is operably engaged with the arm attachment assembly. It is capable of measuring anterior-posterior translations and inferior translations relative to the arm of a patient and includes a girdle connecting element. The girdle assembly is operably engageable with the girdle connecting element. The girdle assembly is capable of being secured to the torso of the patient to provide a fixed point of reference. During application of either an anterior-posterior force or an inferior force to an arm of a patient, glenohumeral joint displacement is measured, the amount of force being registered by the force measurement gauge, while the amount of translation is registered via the translation measurement gauge assembly.

12 Claims, 4 Drawing Sheets

SHOULDER ARTHROMETER

BACKGROUND OF THE INVENTION

1. Field of the Invention

The present invention relates to a device and method for measuring glenohumeral (shoulder) joint translation in the anterior-posterior directions and the inferior direction.

2. Description of the Related Art

The shoulder is the most mobile joint in the body. This mobility allows a significant amount of motion that gives us the ability to throw and perform other overhead activities. Proper shoulder function requires the humeral head to remain relatively centered within the glenoid concavity during active motion. Damage to the soft tissue structures that maintain the joint in place typically leads to an excessive amount of motion, eventually progressing to either a dislocation, where the joint comes completely out, or a subluxation where the joint only partially comes out of place.

The term glenohumeral instability is used to define the symptomatic inability to maintain the humeral head centered in the glenoid fossa. In addition to a detailed history of the patient's problem, a physical examination is the key to successful diagnosis of these problems. In examining a loose joint, the term glenohumeral laxity is used to describe the range of movement of the center of the humeral head with respect to the glenoid concavity while force is applied to the arm.

In cases of suspected shoulder instability, determining the degree of shoulder laxity in the involved shoulder and comparing it with that of the uninvolved shoulder may be helpful in making a diagnosis and determining the necessary treatment. While several authors have described techniques for evaluating and quantifying glenohumeral laxity (Gerber, Hawkins, Matsen), there is no data on clinical measurement of the absolute amount of translation which occurs on examination. (See Gerber C, Ganz R: Clinical assessment of instability of the shoulder. With special reference to anterior and posterior drawer tests. J Bone Joint Surgery, 66B: 551–556, 1984; Hawkins R J, Bokor D J: Clinical evaluation of shoulder problems, in Rockwood Cailf., Matsen F A III (eds): The Shoulder. Volume 1. Philadelphia, WB Saunders Co. 1990, pp 149–177; Matsen F A, Thomas S C, Rockwood Cailf.: Anterior glenohumeral stability, in Rockwood Cailf., Matsen F A III (eds): The Shoulder. Volume 1. Philadelphia, WB Saunders Co. 1990, pp 547–551.)

In the knee, several instruments are available to quantify translation of the joint in order to diagnose instability. These instruments are, for the most part, portable and easy to use by a variety of medical personnel. In sharp contrast to the knee, however, no comparable instrument has been developed to quantify joint laxity in the shoulder. Some studies are available on the absolute measurement of translation. However, these studies have employed instruments that either are to be used by personnel that are highly-skilled in their use, or the instruments are complex and not portable.

One study by Krarup, et al., evaluated the motion of the glenohumeral joint using an ultrasonic transducer. In their study, translation was studied in the anterior to posterior direction. They studied 20 healthy shoulders and 20 with instability. The average translation of the healthy shoulders was 1.9 mm, while that of the unstable shoulders was 4.9 mm. Furthermore, the difference from side to side in those with normal shoulders was 0.7 mm, while the difference in those with instability was 2.8 mm. The authors used a translation force of 90 Newtons to elicit the values quoted. While the variation by one examiner was not significant, they found that the variation between various examiners was significantly different. In summary, this technique certainly allowed for measurement of translation, however, it would need to be performed by a trained ultrasound technologist. (See Krarup A L, Court-Payen M, Skjoldbye B, Lausten G: Ultrasonic measurement of the anterior translation in the shoulder joint. Journal of Shoulder and Elbow Surgery, 8:136–141, 1999.)

Another study by Sidles, et al., has evaluated the amount of glenohumeral translation using a spatial tracking system. In normal shoulders, they found an average translation of between 8 and 11 mm, depending on the direction of testing. The system they employed was one that requires markers to be placed on the patient and the use of several video cameras to record the degree of translation. (See Sidles J A, Harryman D T, Harris S L, Matsen F A: In vivo quantification of glenohumeral stability. Orthopaedic Research Society, $37^{th}$ Annual Meeting, Anaheim, Calif., March 4–7, 1991.)

Finally, Jorgensen & Bak have employed a modified knee laxity tester in the assessment of anterior-posterior (AP) translation of the glenohumeral joint. They found that measurements in this direction were highly reproducible. Additionally, the translation in normal patients was significantly less than in those with instability. In their study a force of 20 pounds was used to reproduce the given translations. This is equivalent to 85 Newtons. This device, however, measured only one plane of motion. (See Jorgensen U, Bak K: Shoulder instability. Assessment of anterior-posterior translation with a knee laxity tester. Acta Orthopaedica Scandinavica, 66: 398–400, 1995.)

U.S. Pat. No. 5,911,695, issued to Watkins, et al., discloses a device for testing the inferior glenohumeral ligament of the shoulder of a patient with the application of a measurable force. This device can measure the anterior to posterior translation of the humeral head relative to the clavicle while a measured force is applied. By virtue of its design, however, it allows for measuring only anterior to posterior motion and cannot be employed to measure any other direction of translation.

As will be disclosed below, the present invention measures the amount of translation that a glenohumeral joint undergoes as a specific force is applied to the arm. The directions of motion that can be quantified include the anterior-posterior and inferior directions. As used herein, the term "anterior-posterior" refers to directions from both the anterior to posterior and from the posterior to anterior. These directions are all important in the measurement of glenohumeral joint laxity.

OBJECTS AND SUMMARY OF THE INVENTION

It is therefore a principal object of the present invention to measure translation of the glenohumeral joint as a specific force is applied to the arm in the anterior-posterior and also the inferior directions.

It is another object to provide highly reproducible measurements of the translation of the glenohumeral joint resulting from consistent forces applied thereto.

Yet another object is to provide reproducible measurements of a glenohumeral joint translation as between varying examiners.

Still another object is to provide a measurement device that is portable.

These and other objects are achieved by the present invention which is a shoulder arthrometer for measuring glenohumeral joint translation upon application of a force to an arm of a patient. In its broad aspects it includes an arm attachment assembly, a force measurement gauge, a translation measurement gauge assembly, and a girdle assembly. The arm attachment assembly is capable of being secured to the arm of a patient. The force measurement gauge is operably engaged with the arm attachment assembly for measuring a force applied to the arm attachment assembly in anterior-posterior directions and the inferior direction. The translation measurement gauge assembly is operably engaged with the arm attachment assembly. It is capable of measuring anterior-posterior translations and inferior translations relative to the arm of a patient and includes a girdle connecting element. The girdle assembly is operably engageable with the girdle connecting element. The girdle assembly is capable of being secured to the torso of the patient to provide a fixed point of reference. During application of either an anterior-posterior force or an inferior, force to an arm of a patient, glenohumeral joint displacement is measured. The amount of force applied measurement gauge, while the amount of translation is registered via the translation measurement gauge assembly.

Other objects, advantages, and novel features will become apparent from the following detailed description of the invention when considered in conjunction with the accompanying drawings.

BRIEF DESCRIPTION OF THE DRAWINGS

The same reference characters designate the same parts or elements throughout the drawings.

DETAILED DESCRIPTION OF THE PREFERRED EMBODIMENTS

Figure 1:
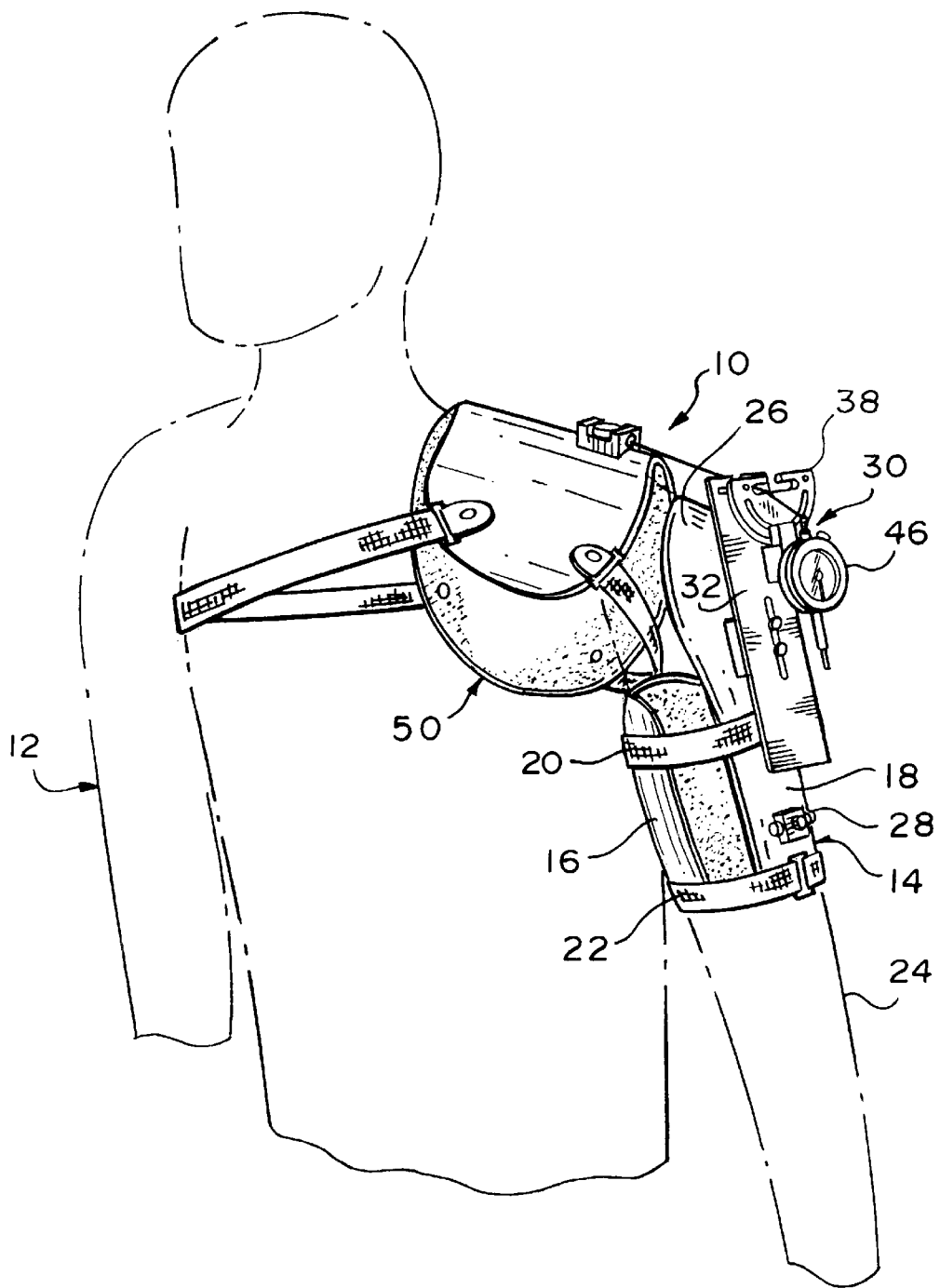
FIG. 1 is a front, left side perspective view of a preferred embodiment of the shoulder arthrometer of the present invention, shown secured to a patient.
Figure 3:
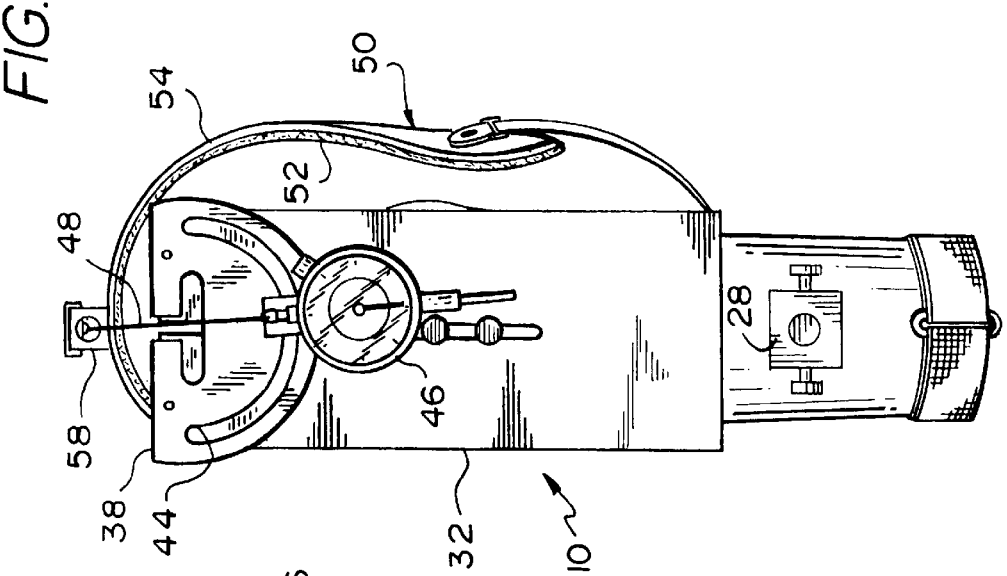
FIG. 3 is an enlarged side perspective view of the shoulder arthrometer.
Figure 2:
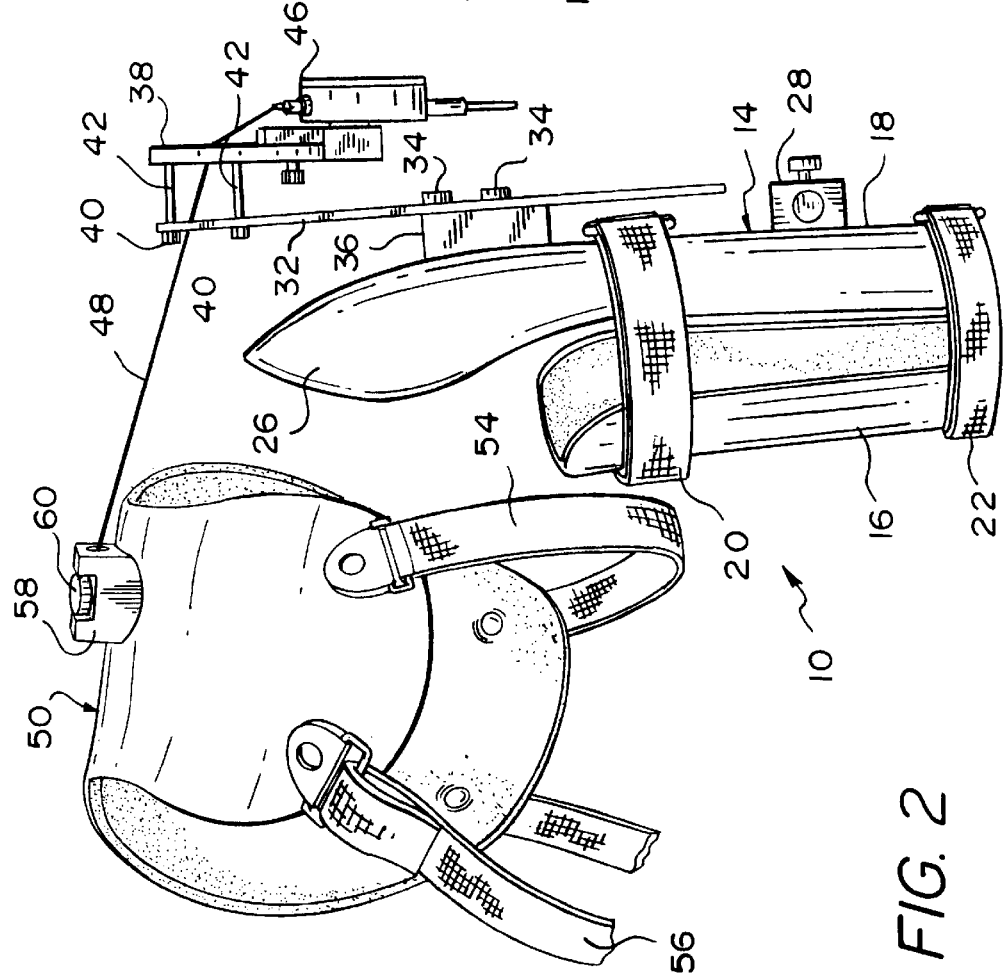
FIG. 2 is an enlarged front perspective view of the shoulder arthrometer.

Referring now to the drawings and the characters of reference marked thereon, FIG. 1 illustrates a preferred embodiment of the present invention, designated generally as 10, shown secured to the torso of a user patient 12.

The shoulder arthrometer 10 includes an arm attachment assembly, designated generally as 14. The arm attachment assembly 14 includes a medial arm attachment section 16, a lateral arm attachment section 18, and adjustable arm attachment means 20, 22. The medial arm attachment section 16 approximates the shape of the upper medial portion of the arm of the patient 12. The lateral arm attachment section 18 approximates the shape of the upper lateral portion of the arm of the patient 12. The adjustable arm attachment means 20, 22 are operably engaged with the medial arm attachment section 16 and the lateral arm attachment section 18 for securing the medial and lateral arm attachment sections to the upper arm of the patient 12.

Attachment sections 16, 18 are preferably formed of molded plastic. The lateral arm attachment section 18 preferably includes an upper edge portion 26 that approximates the shape of the patient's deltoid muscle.

The upper edge portion 26 is optional and may not be included in the device for it to be functional. In that situation, the attachment section 18 may be similar to the attachment section 16. In another alternative, the arm attachment sections 16 and 18 may be formed by one solid portion which may contain an air bladder similar to that employed in a blood pressure cuff.

Each arm attachment means 20, 22 is preferably a VELCRO™ strap. The straps 20, 22 are anchored to the lateral arm attachment section 18 and are passed through eyelets (not shown) on the medial arm attachment section 16. They are then affixed at the lateral arm attachment section 18.

A force measurement gauge 28 is operably engaged with the arm attachment assembly for measuring a force applied to the arm attachment assembly 14 in anterior-posterior directions and the inferior direction. The preferred value for a maximum force applied which would result in an adequate translation of the glenohumeral joint is 90 Newtons. Generally, forces greater than this would not result in additional translation of glenohumeral joint. The maximum value that the force measurement gauge 28 will register should therefore be at least about 90 Newtons. Such a force measurement gauge 28 may be commercially available as a spring calibrated tensiometer. Such a tensiometer generally comprises a simple spring with a specific tension. It is commonly referred to as a "fish scale". Alternatively, an electronic device known as a load cell, also commercially available may be used for this purpose.

A translation measurement gauge assembly, designated generally as 30, is attached to the arm attachment assembly 14. The translation measurement gauge assembly 30 is capable of measuring anterior-posterior translations and inferior translations relative to the arm of the patient. The translation measurement gauge assembly 30 includes a housing 32 securely attachable to the arm attachment assembly 14 by a sliding screwbar 36. Screwbar 36 is securely attached, at one side, to the arm attachment assembly 14 and adjustably attached to the housing 32, via finger nuts 34.

A sliding attachment member 38 is securely connected to the housing 32 via screws 40 and tubular spacers 42. The sliding attachment member has a track 44 formed therein. A translation measurement gauge 46 is slideably connected to the sliding attachment member 38 via the track 44 for positioning the translation measurement gauge 46 in the appropriate position to allow translation measurements in the positions of forward flexion, extension, abduction and external rotation. The translation measurement gauge 46 is commercially available for example, from Space Age Control, Inc., Series 150, Model No. 150-0121. It is sold as an analog-output ultra-small position transducer. A number of mechanical gauges which are also readily available commercially could also serve the purpose. The translation measurement gauge assembly 30 includes a girdle connecting element 48, i.e. adjustable wire or cable, which attaches at a first end to the translation measurement gauge 46.

A girdle assembly, designated generally as 50, is operably engageable with a second end of the girdle connecting element 48. The girdle assembly 50 is capable of being secured to the torso of the patient to provide a fixed point of reference.

The girdle assembly 50 includes a main girdle. The main girdle includes an inner shell 52 and an outer shell 54. The inner shell 52 approximates the contour of the patient's shoulder. The inner shell 52 is preferably formed of a relatively soft material such as a closed cell polyethylene polymer commercially available as Plastizote™. This material can conform to the shoulder contour. The outer shell 54 is positioned over the inner shell 52. The outer shell 54 is preferably formed of a rigid polyethylene material commercially available under the trademark Orthoplast™. This rigidity optimizes the girdle assembly's function of providing a fixed point of reference.

First adjustable girdle attachments means, i.e. strap 54, is securable about the patient's axilla and attached to the main girdle. Second adjustable girdle attachments means, i.e. strap 56, is securable around the patient's body and attached to the main girdle.

Although not shown in these figures the girdle assembly 50 may include expansion capabilities for larger patients. Such expansion features may include appropriate sliding attachments.

The girdle assembly, further includes an attachment device 58 that is secured to the outer shell 54 and attachable to the girdle connecting element 48. The attachment device 58 will allow for positioning the girdle connecting element 48 at variable lengths, depending on the position of the arm, through finger nut 60.

In operation, the method of measuring glenohumeral joint translation utilizing the shoulder arthrometer is as follows:

The girdle assembly 50 is secured to the torso of the patient via straps 54 and 56. The girdle attachment device 58 serves as a point of reference for the glenohumeral joint translation measurements.

The arm attachment assembly 14 is then secured to the arm of the patient 12 by means of adjustable straps 20 and 22. The arm attachment assembly 14 has the translation measurement gauge assembly 30 attached thereto. The translation measurement gauge assembly 30 is capable of measuring anterior-posterior and inferior translations relative to the girdle assembly 50. This measurement therefore is an indirect measurement of the glenohumeral translation taking place.

The translation measurement gauge assembly 30 is adjusted for appropriate arm positioning. This is performed by adjusting the height of the translation measurement gauge assembly 30 by loosening finger nuts 34 and sliding the housing 32 up or down depending on its position relative to the glenohumeral joint. Sliding the translation measurement gauge 46 along the track 44 of the sliding attachment member 38 may perform an additional adjustment for rotation of the arm.

Beginning with the arm in the desired position, a force is applied to the arm of the patient 12. The direction of the force can be in the anterior to posterior direction, the posterior to anterior direction or the inferior direction, depending on the direction desired by the examiner. The force is measured by utilizing the force measurement gauge 28 operably engaged with the arm attachment assembly 14. The resulting glenohumeral joint translation is measured by reading the value from the translation measurement gauge 46.

The process is repeated by repositioning the arm of the patient 12, in the new position, applying the force in the desired direction by applying force to the force measurement gauge 28 and reading the amount of translation from the translation measurement gauge 46. Any combination of anterior to posterior, posterior to anterior and inferior forces can be applied with the arm in any position and the force measurement gauge 28 will document the amount of force while the translation measurement gauge 46 will register the amount of glenohumeral translation.

Figure 4:
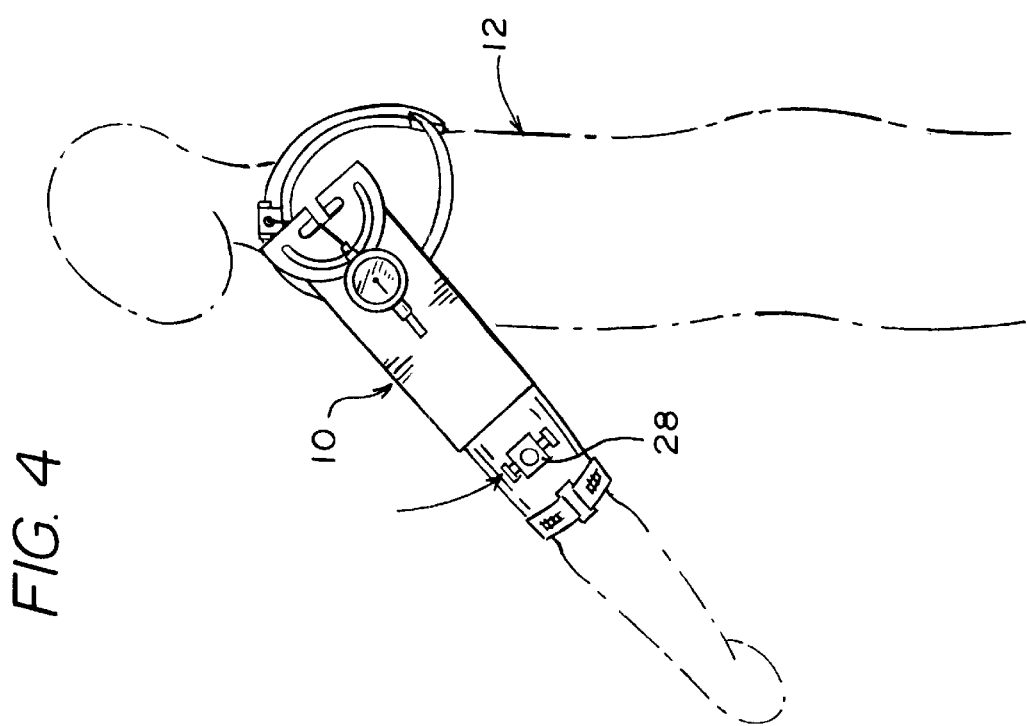
FIG. 4 is a side perspective view of the shoulder arthrometer shown secured to a patient with the arm in forward flexion.

Referring now to FIG. 4, the arm of the patient 12 is shown positioned at about 45 degrees of forward flexion after the arm attachment assembly 14 and girdle assembly 50 are secured to the patient. The beginning position of the translation measurement gauge 46 is noted prior to applying the force. An anterior to posterior force, designated by the arrow, is applied to the arm of the patient 12 at the force measurement gauge 28. Once a force approaching about 90 Newtons has been applied to the force measurement gauge 28, the value will be evident on the device. The value of the translation can be read from the translation measurement gauge 46.

Figure 5:
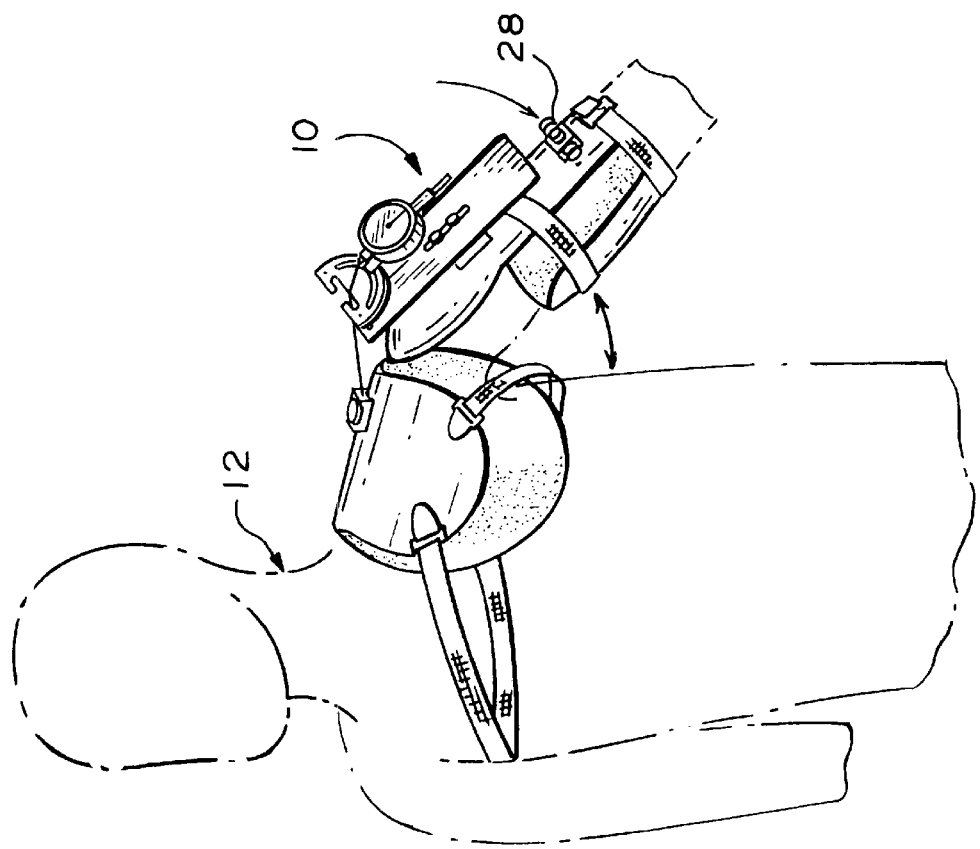
FIG. 5 is a front, left perspective view showing the arm in abduction.

Referring now to FIG. 5, the arm of the patient 12 is positioned at about 45 degrees of abduction. An anterior to posterior force, designated by the arrow is applied to the arm of the patient 12 at the force measurement gauge 28. Once a force approaching about 90 Newtons has been applied to the force measurement gauge 28, the value will be evident on the device. The value can now be read from the translation measurement gauge 46.

Obviously, many modifications and variations of the present invention are possible in light of the above teachings. For example, although the force measurement gauge 28 has been shown located on the arm attachment assembly 14 it could be positioned on the translation measurement gauge assembly 30, and, in that location, be deemed operably engaged with the arm attachment assembly 14. Also, although the translation measurement gauge assembly 30 has been shown located on the arm attachment assembly 14, it could be positioned on the girdle assembly 50 with the girdle attachment device 58 being secured to the arm attachment assembly 14. It is, therefore, to be understood that within the scope of the appended claims, the invention may be practiced otherwise than as specifically described.

What is claimed and desired to be secured by Letters Patent of the United States is:

1. A shoulder arthrometer for measuring glenohumeral joint translation upon application of a force to an arm of a patient, comprising:
   a) an arm attachment assembly capable of being secured to the arm of a patient;
   b) a force measurement gauge operably engaged with said arm attachment assembly for measuring a force applied to the arm attachment assembly in anterior-posterior directions and the inferior direction;
   c) a translation measurement gauge assembly operably engaged with said arm attachment assembly, said translation measurement gauge assembly being capable of measuring anterior-posterior translations and inferior translations relative to the arm of a patient, said translation measurement gauge assembly including a girdle connecting element; and,
   d) a girdle assembly operably engageable with said girdle connecting element, said girdle assembly being capable of being secured to the torso of the patient to provide a fixed point of reference,
   wherein during application of either an anterior-posterior force or an inferior force to an arm of a patient, glenohumeral joint displacement is measured, the amount of force being registered by said force measurement gauge, while the amount of translation is registered via said translation measurement gauge assembly.

2. The shoulder arthrometer of claim 1, wherein said arm attachment assembly, comprises
   a) a medial arm attachment section approximating the shape of the upper medial portion of an arm of a patient;

b) a lateral arm attachment section approximating the shape of the upper lateral portion of an arm of a patient; and, c) adjustable arm attachment means operably engaged with said medial arm attachment section and said lateral arm attachment section for securing said medial and lateral arm attachment sections to the upper arm of the patient.

3. The shoulder arthrometer of claim 2, wherein said lateral arm attachment section includes an upper edge portion which approximates the shape of a patient's deltoid muscle.

4. The shoulder arthrometer of claim 1, wherein said girdle assembly, comprises a main girdle, said main girdle, comprising:

a) an inner shell approximating the contour of the patient's shoulder, said inner shell being formed of a relatively soft material that allows it to conform to the shoulder contour; and, b) an outer shell positioned over said inner shell, being formed of a relatively rigid material to optimize the girdle assembly's function of providing said fixed point of reference.

5. The shoulder arthrometer of claim 4, wherein said girdle assembly, further comprises:

a) a first adjustable girdle attachment means securable about the patient's axilla and attached to said main girdle; and, b) a second adjustable girdle attachment means securable around the patient's body and attached to said main girdle.

6. The shoulder arthrometer of claim 4, wherein said girdle assembly, further comprises an attachment device secured to said main girdle and attachable to said girdle connecting element.

7. The shoulder arthrometer of claim 1, wherein said girdle connecting element comprises an adjustable cable attached at a first end to said translation measurement gauge assembly and at a second end to said attachment device.

8. The shoulder arthrometer of claim 1, wherein said translation measurement gauge assembly, comprises:

a) a housing securely attachable to said arm attachment assembly;

b) a sliding attachment member securely connected to said housing, said sliding attachment member having a track formed therein; and, c) a translation measurement gauge slideably connected to said sliding attachment member via said track for positioning the translation measurement gauge in the appropriate position to allow translation measurements in the positions of forward flexion, extension, abduction and external rotation.

9. The shoulder arthrometer of claim 7, wherein said housing is securely attachable to said arm attachment assembly by a sliding screwbar which is securely attached at one side to the arm attachment assembly and adjustably attached to the housing via a plurality of nuts.

10. The shoulder arthrometer of claim 1, wherein said translation measurement gauge is attached to said arm attachment assembly.

11. The shoulder arthrometer of claim 7, wherein said girdle assembly is attached to said girdle connecting element.

12. A method for measuring glenohumeral joint translation upon application of a force to an arm of a patient, comprising the steps of:

a) securing a girdle assembly to the torso of the patient to provide a fixed point of reference;

b) securing an arm attachment assembly to the arm of a patient, said arm attachment assembly having a translation measurement gauge assembly attached thereto, said translation measurement gauge assembly being capable of measuring anterior-posterior translations and inferior translations relative to the arm of a patient, said translation measurement gauge assembly including a girdle connecting element, said girdle connecting element being operably engageable with said girdle assembly;

c) adjusting said translation measurement gauge assembly for appropriate arm positioning to allow translation measurements in desired degrees of forward flexion, extension, abduction and external rotation;

d) applying an anterior-posterior force to the arm of a patient;

e) measuring the anterior-posterior force by utilizing a force measurement gauge operably engaged with said arm attachment assembly;

f) measuring the resulting glenohumeral joint translation by utilizing said translation measurement gauge assembly;

g) applying an inferior force to the arm of the patient;

h) measuring the inferior force by utilizing said force measurement gauge; and i) measuring the resulting glenohumeral joint translation by utilizing said translation measurement gauge assembly.

* * * * *